United States Patent
Mougiakakou et al.

(10) Patent No.: US 10,937,536 B2
(45) Date of Patent: Mar. 2, 2021

(54) ESTIMATION OF INSULIN BASED ON REINFORCEMENT LEARNING

(71) Applicant: UNIVERSITÄT BERN, Berne (CH)

(72) Inventors: Stavroula Mougiakakou, Bern (CH); Eleni Daskalaki, Neuchâtel (CH); Peter Diem, Berne (CH)

(73) Assignee: UNIVERSITÄT BERN, Berne (CH)

( * ) Notice: Subject to any disclaimer, the term of this patent is extended or adjusted under 35 U.S.C. 154(b) by 51 days.

(21) Appl. No.: 16/318,015

(22) PCT Filed: Jul. 14, 2017

(86) PCT No.: PCT/IB2017/054283
§ 371 (c)(1),
(2) Date: Jan. 15, 2019

(87) PCT Pub. No.: WO2018/011766
PCT Pub. Date: Jan. 18, 2018

(65) Prior Publication Data
US 2019/0214124 A1    Jul. 11, 2019

(30) Foreign Application Priority Data
Jul. 15, 2016    (WO) .................. PCT/IB2016/054242

(51) Int. Cl.
*G16H 20/17* (2018.01)
*G16H 50/50* (2018.01)
(Continued)

(52) U.S. Cl.
CPC ......... *G16H 20/17* (2018.01); *A61B 5/14532* (2013.01); *A61B 5/7282* (2013.01);
(Continued)

(58) Field of Classification Search
CPC ........ G16H 50/20; G16H 50/50; G16H 20/17; G16H 20/00; G06N 7/00; A61B 5/14532; G61B 5/7282
(Continued)

(56) References Cited

U.S. PATENT DOCUMENTS

| | | | |
|---|---|---|---|
| 2005/0272640 A1* | 12/2005 | Doyle, III | G16H 20/10 435/14 |
| 2017/0277841 A1* | 9/2017 | Shankar | G06F 19/00 |

FOREIGN PATENT DOCUMENTS

| | | | |
|---|---|---|---|
| WO | 2015/067956 | 5/2015 | |
| WO | WO-2015067956 A1 * | 5/2015 | ...... A61M 5/1723 |

OTHER PUBLICATIONS

Mariano De Paula et al.: "Controlling Blood Glucose Variability Under Uncertainty Using Reinforcement Learning and Gaussian Processes", Applied Soft Computing, vol. 35, Oct. 2015 (Oct. 1, 2015), pp. 310-332, XP055418575, Amsterdam, NL, ISSN: 1568-4945 (Year: 2015).*

(Continued)

*Primary Examiner* — Joy Chng
(74) *Attorney, Agent, or Firm* — Nixon & Vanderhye P.C.

(57) ABSTRACT

The optimal insulin to be delivered by an insulin infusion pump is determined by using a reinforcement learning algorithm aiming to the personalized glucose regulation. The algorithm optimizes the daily basal insulin rate and insulin: carbohydrate ratio for each patient, on the basis of his/her measured glucose profile. The proposed algorithm is able to learn in real-time patient-specific characteristics captured in the daily glucose profile and provide individualized insulin treatment. An automatic and personalized tuning method contributes in the optimisation of the algorithm's performance.

20 Claims, 5 Drawing Sheets

(51) Int. Cl.
*G16H 50/20* (2018.01)
*G06N 20/00* (2019.01)
*A61B 5/145* (2006.01)
*A61B 5/00* (2006.01)
*G06N 7/00* (2006.01)

(52) U.S. Cl.
CPC ............... *G06N 7/00* (2013.01); *G06N 20/00* (2019.01); *G16H 50/20* (2018.01); *G16H 50/50* (2018.01)

(58) Field of Classification Search
USPC ........................................................ 705/2–3
See application file for complete search history.

(56) References Cited

OTHER PUBLICATIONS

Daskalaki Elena et al.: "Personalized Tuning of a Reinforcement Learning Control Algorithm for Glucose Regulation", Engineering in Medicine and Biology Society (EMBC), 2013 35th Annual International Conference of the IEEE, IEEE, Jul. 3, 2013 (Jul. 3, 2013), pp. 3487-3490, XP032488359, ISSN: 1557-170 (Year: 2013).*
Mariano De Paula et al.: "Controlling Blood Glucose Variability Under Uncertainty Using Reinforcement Learning and Gaussian Processes", Applied Soft Computing, vol. 35, Oct. 2015 (Oct. 1, 2015), pp. 310-332, XP055418575, Amsterdam, NL, ISSN: 1568-4945 (Year: 2013).*
Mariano De Paula et al.: "On-line Policy Learning and Adaptation for Real-Time Personalization of an Artificial Pancreas", Expert Systems With Applications, vol. 42, No. 4, Mar. 1, 2015 (Mar. 1, 2015), pp. 2234-2255. XP055418564, GB ISSN: 0957-4174 ( Year: 2015).*
International Search Report for PCT/IB2017/054283, dated Nov. 9, 2017, 4 pages.
Written Opinion of the ISA for PCT/IB2017/054283, dated Nov. 9, 2017, 6 pages.
M. De Paula et al., "Controlling blood glucose variability under uncertainty using reinforcement learning and Gaussian processes", Applied Soft Computing, vol. 35, Oct. 1, 2015, pp. 310-332.
D.Elena et al., "Personalized tuning of a reinforcement learning control algorithm for glucose regulation", Engineering in Medicine and Biology Society (EMBC), 2013 35th Annual International Conference of the IEEE, IEEE, Jul. 3, 2013, pp. 3487-3490.
M. De Paula et al., "On-line policy learning and adaptation for real-time personalization of an artificial pancreas", Expert Systems With Applications, vol. 42, No. 4, Mar. 1, 2015, pp. 2234-2255.
Bhatnagar, Shalabh, et al., "Natural Actor-Critic Algorithms," Automatica, vol. 45, No. 11, Jun. 2009, 38 pages.
Butte, A. J., et al., "Mutual Information Relevance Networks: Functional Genomic Clustering Using Pairwise Entropy Measurements," Pacific Symposium on Biocomputing 5, 2000, pp. 415-426.
Greensmith, Evan, et al., "Variance Reduction Techniques for Gradient Estimates in Reinforcement Learning," Journal of Machine Learning Research 5, 2004, pp. 1471-1530.
Grondman, Ivo, et al., "A Survey of Actor-Critic Reinforcement Leaning: Standard and Natural Policy Gradients," IEEE Transactions on Systems, Man and Cybernetics, Part C: Applications and Reviews, vol. 42, No. 6, 2012, 17 pages.
Konda, Vijay R., et al., "On Actor-Critic Algorithms," Siam J. Control Optim., vol. 42, No. 4, 2003, pp. 1143-1166.
Lee, Hyunjin, et al., "A Closed-Loop Artificial Pancreas Using Model Predictive Control and a Sliding Meal Size Estimator," Journal of Diabetes Science and Technology, vol. 3, Issue 5, Sep. 2009, pp. 1082-1090.
Marbach, Peter, et al., "Simulation-Based Optimization of Markov Reward Processes," IEEE Transactions on Automatic Control, vol. 46, No. 2, 2001, pp. 191-209.
Peters, Jan, et al., "Natural Actor Critic," Neurocomputing 71, 2008, pp. 1180-1190.
Schiavon, Michele, et al., "Quantitative Estimation of Insulin Sensitivity in Type 1 Diabetic Subjects Wearing a Sensor-Augmented Insulin Pump," Diabetes Care, vol. 37, May 2014, pp. 1216-1223.
Si, Jennie, et al. (Editors), "Handbook of Learning and Approximate Dynamic Programming," vol. 2, 2004, 30 pages.
Sutton, Richard S., "Learning to Predict by the Methods of Temporal Differences," Machine Learning 3, 1988, pp. 9-44.
Tsitsiklis, John N., et al., "An Analysis of Temporal-Difference Learning with Function Approximation," IEEE Transactions on Automatic Control, vol. 42, No. 5, May 1997, pp. 674-690.
Turksoy, Kamuran, et al., "Adaptive Control of Artificial Pancreas Systems—A Review," Journal of Healthcare Engineering, vol. 5, No. 1, 2014, pp. 1-22.
Walsh, John, et al., "Guidelines for Insulin Dosing in Continuous Subcutaneous Insulin Infusion Using New Formulas from a Retrospective Study of Individuals with Optimal Glucose Levels," Journal of Diabetes Science and Technology, vol. 4, Issue 5, Sep. 2010, pp. 1174-1181.
Williams, Paul L., et al., "Generalized Measures of Information Transfer," 2011, arXiv preprint arXiv:1102.1507, 6 pages.
Daskalaki et al., "An Actor-Critic based controller for glucose regulation in type 1 diabetes" *Computer Methods and Programs in Biomedicine*, vol. 109, No. 2: 116-25 (2013).

* cited by examiner

ESTIMATION OF INSULIN BASED ON REINFORCEMENT LEARNING

This application is the U.S. national phase of International Application No. PCT/IB2017/054,283 filed 14 Jul. 2017, which designated the U.S. and claims priority to International Patent Application No. PCT/IB2016/054,242 filed 15 Jul. 2016, the entire contents of each of which are hereby incorporated by reference.

TECHNICAL FIELD

The invention relates to the field of administration of insulin and to a corresponding Artificial Pancreas.

BACKGROUND OF THE INVENTION

Type 1 diabetes (T1D) is a metabolic disease characterised by uncontrolled blood glucose levels, due to the absence or malfunction of insulin. The Artificial Pancreas (AP) system aims to simulate the function of the physiological pancreas and serve as an external automatic glucose regulation system. AP combines a continuous glucose monitor (CGM), a continuous subcutaneous insulin infusion (CSII) pump and a control algorithm which closes the loop between the two devices and optimises the insulin infusion rate.

An important challenge in the design of efficient control algorithms for AP is the use of the subcutaneous route both for subcutaneous glucose measurement and subcutaneous insulin infusion; this introduces delays of up to 30 minutes for subcutaneous glucose measurement and up to 20 minutes for insulin absorption. Thus, a total delay of almost one hour restricts both monitoring and intervention in real time. Moreover, glucose is affected by multiple factors, which may be genetic, lifestyle and environmental. With the improvement in sensor technology, more information can be provided to the control algorithm (e.g. more accurate glucose readings and physical activity levels); however, the level of uncertainty remains very high. Last but not least, one of the most important challenges emerges from the high inter- and intra-patient variability, which dictates personalized insulin treatment.

Along with hardware improvements, the challenges of the AP are gradually being addressed with the development of advanced algorithmic strategies; the strategies most investigated clinically are the Proportional Integral Derivative (PID)], the Model Predictive Controller (MPC) and fuzzy logic (e.g. MD-Logic) algorithms. A recent development has been the bi-hormonal AP, which uses both insulin and glucagon. The increasing number of clinical trials has led to extensive in-hospital and, more recently, at-home evaluation of the feasibility of AP outside the controlled hospital environment. Most studies are restricted to the algorithmic evaluation of a patient cohort under uncertain conditions, such as erroneous meal intake and insulin sensitivity (SI) changes (e.g. physical activity).

In spite of these promising results, none of the currently proposed control strategies is intrinsically designed to handle uncertainties and personalization. PID is designed for linear systems, MPC solves an open-loop optimisation problem which has proved sub-optimal in the presence of uncertainty and MD-Logic is a rule-based approach directly subjected to the experience of the designer. In the view of patient variability, the algorithms have been enhanced with adaptive components, which are mainly based on the personalized identification of models involved or correlation of algorithmic parameters with one or multiple patient-specific characteristics, such as body weight, correction factor or SI. Nevertheless, the successful performance of the state-of-the-art AP algorithms proves that AP development is both feasible and viable and paves the path to a new era of more advanced algorithmic research towards robust and personalized insulin treatment.

Reinforcement learning (RL) is a branch of machine learning (ML) and is an intensively active research field which embraces algorithms that are able to learn from data and perform optimisation within uncertain environments. The field of RL falls between supervised and unsupervised learning and includes problems where an agent attempts to improve its performance at a given task over time by continual interaction with its environment. During this effort, no input-output data are explicitly provided, and the performance improvement is translated as minimizing some notion of long-term expected cost over the path of the agent. RL began to develop as an independent branch in the early 1980s and was inspired by animal psychology and the idea of learning through trial-and-error. It was quickly adopted by the field of optimal control as a very efficient way to solve dynamic programming problems for which Bellman's "curse of dimensionality" restricted an analytical solution. In RL, the agent follows a certain control policy based on which it choses actions u and moves from the current state x to the next. Each state transition is followed by a local cost c which denotes the quality of this transition based on some predefined criteria. Aim of the agent is to find an optimal control policy so as to minimize the total expected cost throughout its path. RL is a field with an extensively investigated theoretical background, which is now finding its way towards practical application, due to modern advances in computational capacity. In this view, the application in real life problems is highlighted as one of the current trends of RL. In medicine, RL is mainly investigated for prognosis, classification and diagnosis by means of big/heterogeneous data collection, fusion and analysis, with fewer reports on treatment studies. The advantages of ML and RL illustrate a promising path towards the resolution of the AP challenges, as has been recently recognised and reported. To evaluate the algorithm, a deterministic glucoregulatory model was used, but augmented with uncertainty to simulate patient variability. This process may not be representative of actual patient variability and limits the strength of the adaptive capability presented.

One factor that complicates the use of RL in medicine is the high number of constant and adaptive parameters which need to be tuned or initialized. Choosing the optimal values for these parameters is a challenging task and is usually performed manually, on the basis of problem-specific characteristics. However, in the face of inter-individual variability, this manual process may be unreliable or even unfeasible. Yet another criticism of RL is the difficulty in generalisation or qualitative explanation of both the learning process and the final solution (black box).

In the present approach, an RL-based algorithm is proposed for personalized insulin infusion and glucose regulation in T1D. A model-free Actor-Critic (AC) algorithm is developed and evaluated in silico for its ability to maintain normoglycaemia within a large patient cohort and under variable environmental uncertainties. The scope of the approach is two-fold:
  i) to investigate the applicability of RL in the context of a personalized AP and
  ii) to achieve an AC design that can be generalised and directly translated to medical experience.

In order to overcome the tuning constraint discussed previously, the AC algorithm is enhanced with a novel method for automatic and personalized tuning, based on the estimation of information transfer (IT) from insulin to glucose signals.

Early-stage work in AC algorithms has already been presented, together with preliminary evaluation results:

Daskalaki E, Diem P, Mougiakakou S. An Actor-Critic based controller for glucose regulation in type 1 diabetes. Comput Methods Programs Biomed. 2013; 109 (2)116-25.

Daskalaki E, Diem P, Mougiakakou S. Personalized tuning of a reinforcement learning control algorithm for glucose regulation, Proceedings of the 35th IEEE Eng Med Biol Soc Conference; 2013 Jul. 3-7; Osaka, Japan.

The entire disclosures of both articles are incorporated herein by reference. In the present invention, a novel design for the AC controller is introduced. Specifically:

The control policy has been augmented by an exploratory policy, in order to increase the search space of the algorithm.

A supervisory control policy has been incorporated to enhance the algorithm's safety.

The AC controller is directly linked to physiological parameters and/or actions drawn from medical experience.

The automatic tuning method has been extended and associated to patient-specific characteristics.

In summary, the proposed novel control scheme is able to meet the following challenges:

Inter-/intra-patient variability and personalization of insulin treatment through the use of a real-time adaptive learning algorithm Robustness from using a control algorithm which is suitable for optimisation under uncertainty Easy transfer to practice in hospital and at home since it is
  based on limited a priori assumptions that counteract the high inter-patient variability
  initialized on the basis of physiological parameters

SUMMARY OF THE INVENTION

The invention provides a method for estimating an optimal therapy, for example, the optimal insulin to be delivered by an insulin delivery device such as an infusion pump. The therapy may be determined by using a reinforcement learning algorithm aiming to the personalized glucose regulation. The algorithm may optimize the daily basal insulin rate and insulin to carbohydrate ratio for each patient, on the basis (for example) of his/her measured glucose profile. Such algorithm may able to learn in real-time patient-specific characteristics captured in the daily glucose profile and provide individualized insulin treatment. An automatic and personalized tuning method contributes in the optimisation of the algorithm's performance. It is worth noting that the design of the algorithm may permits its direct use by the patient without any intervention or intermediate steps involving either physicians or engineers.

For example, during the first four operation days, the system provides the patient's standard treatment as defined by his/her physician and, in parallel, may collect his/her continuous glucose monitor and insulin pump data. At the end of this period, the algorithm automatically initializes several parameters. In sequence, the algorithm may continue the personalization of insulin treatment with daily adaptation of the daily basal insulin rate and insulin-carbohydrate ratio, Preferentially, for all involved calculations, the algorithm needs minimal computational time and can run smoothly on a mobile/portable device.

One of aspects of the invention is a method for determining an insulin therapy for a patient. This method may comprise the following steps:

use a reinforcement learning algorithm to operate an adaptive controller, the reinforcement learning algorithm comprising:
  a. a critic which evaluates an insulin control policy (S) including at least one of an insulin infusion rate and an insulin to carbohydrate ratio, and
  b. an actor which improves the insulin control policy (S);
apply, over a predetermined period of time (k−1), a predetermined insulin control policy ($S_{k-1}$);
collect, over the predetermined period of time (k−1), blood glucose data or profile of the patient;
determine a state of the glucose-regulatory system based, for example, on the collected blood glucose data;
evaluate by the critic the predetermined insulin control policy ($S_{k-1}$) based, for example, on the state of the glucose-regulatory system;
update by the actor, the insulin control policy (S), based, for example, on a determined control action, wherein the updated insulin control policy ($S_K$) is intended to apply over a subsequent period of time (k);

The determined control action takes into account at least one of the following control actions:
  a linear deterministic control action ($P_a$);
  a supervisory control action ($P_s$), and
  an exploratory control action ($P_e$).

The linear deterministic control action ($P_a$) may be defined as a linear combination of the glucose-regulatory system's state and a determined policy parameter vector. The supervisory control action ($P_s$) may correspond to a conservative suggestion of a previous insulin control policy. It may act as safety module against extreme changes of the insulin control policy (S) by the algorithm and/or as guidance of the direction of the update. The exploratory control action ($P_e$) may allow widening the search space of the glucose-regulatory system's state and/or supports a faster converge.

Preferentially, the evaluation step is performed at an end of each period of time and the policy parameter vector may be updated at the end of the determined period of time. Furthermore, the duration of the predetermined period of time and/or of the subsequent period of time may be comprised between 1 hour and 36 hours, preferentially substantially equal to 24 hours.

The determined control action may be defined as a rate of change of the insulin control policy (S) from the predetermined period of time (k−1) to the subsequent period of time (k).

The determined control action may take into account at least two of the linear deterministic control action ($P_a$) the supervisory control action ($P_s$) and the exploratory control action ($P_e$).

The determined control action may take into account a total deterministic control action ($P_d$) which is determined by means of a mathematical model that takes into account the linear deterministic control action ($P_a$) and the supervisory control action ($P_s$). Preferentially, the exploratory control action ($P_e$) is determined by means of a mathematical model that takes into account at least the total deterministic control action ($P_d$). The policy parameter vector may depend on the difference between the total deterministic control action ($P_d$) and the exploratory control action ($P_e$).

The critic may evaluate the state of the glucose-regulatory system as described by two features related to the hyper- and hypoglycaemic status occurred during the predetermined period of time (k−1). Furthermore, the critic may evaluate the state of the glucose-regulatory system as described by the average daily hypoglycaemia and hyperglycaemia error occurred during the predetermined period of time (k−1).

Preferentially, the critic computes a local cost of the state of the glucose-regulatory system for the predetermined period of time. And, the actor may be configured to minimize the average expected cost per state.

An initial insulin control policy may be determined by taking into account the patient's individual values as optimized by his/her physician and/or an in silico simulator. The value or the initial value of the policy parameter vector may be determined by using an insulin-to-glucose transfer entropy calculation. Furthermore, the insulin-to-glucose transfer entropy may be estimated on the basis of blood glucose data and insulin delivery data for duration of a time period comprised between 1 and 7 days, preferentially 4 days.

The method may comprise an initialization phase during which an initial insulin control policy and/or an initial value of the policy parameter vector may be determined and adapted to the patient. And the duration of the initialization phase may be comprised between 1 and 7 days, preferentially 4 days.

BRIEF DESCRIPTION OF THE DRAWINGS

The invention will be better understood in view of the description of preferred embodiments and in reference to the figures, wherein.

DETAILED DESCRIPTION OF PREFERRED EMBODIMENTS

The invention is set forth and characterized in the independent claims, while the dependent claims describe other characteristics of the invention.

The present application claims the benefit of the priority of PCT/IB2016/054242 filed on Jul. 15, 2016 in the name of University Bern, the entire disclosure of which is incorporated herein by reference.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to".

As used in this specification and the appended claims, the term "or" is generally employed in its sense including "and/or" unless the content clearly dictates otherwise.

Figure 1:
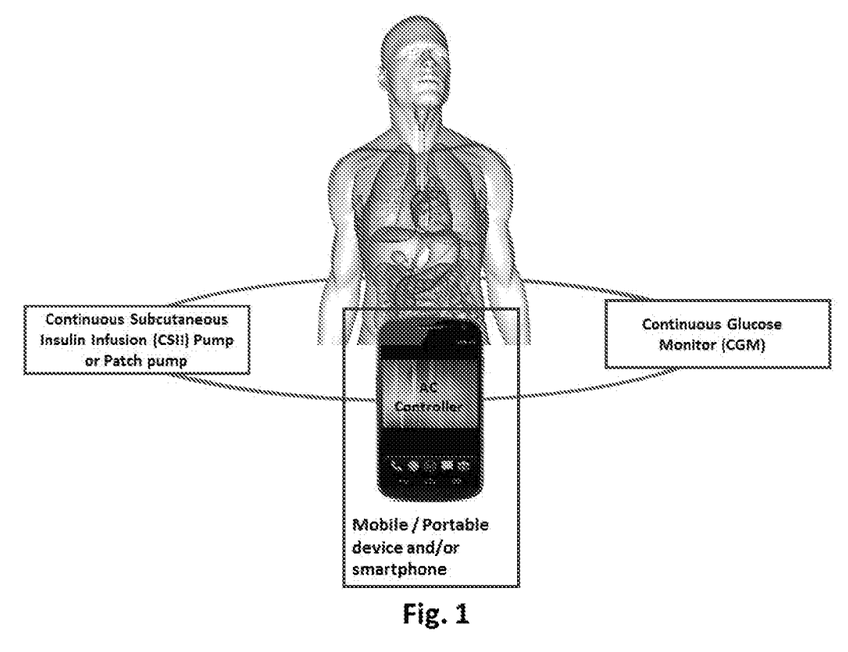
FIG. 1 illustrates the system, artificial pancreas, in which the control system for the pump or patch pump is integrated into a portable device wirelessly connected to both continuous glucose monitor (s) and insulin pump for the real-time transmission of data.

The Actor-Critic control system for closing the loop between continuous glucose monitors and insulin infusion pumps, as illustrated in FIG. 1, may run on any one of a portable/mobile device and smartphone, and is presented in the following paragraphs.

The Actor-Critic Algorithm

Figure 2:
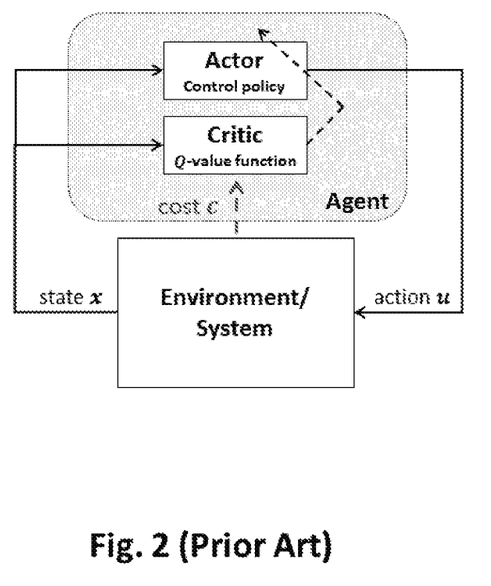
FIG. 2 is a block diagram illustrating the general implementation of the actor-critic control system of FIG. 1 for the implementation of the closed-loop system according to the prior art.

The AC algorithm belongs to the class of RL and is characterised by the separation of the agent into two complementary parts shown in FIG. 2: the Critic, which is responsible for evaluating the control policy and the Actor, which is responsible for improving control policy. Within the RL family, the AC algorithms differ from actor-only or critic-only methods in that they possess better convergence properties. Moreover, their computational cost is lower, as they intrinsically estimate low variance gradients and parameterize policy to allow continuous time optimisation.

In AC learning, the agent follows a specific control policy and performs transitions between states within an uncertain environment. FIG. 2 shows a schematic view of a system controlled by an AC algorithm.

In the case of stochastic systems, the control policy is a conditional probability function $\mu(u|x,\theta)$ from which control actions u are withdrawn, given current states of x. The aim of the agent is to find an optimal control policy, in order to minimise the expected cost throughout its path. Transition between states x and y depends on the chosen control action u and follows a transition probability distribution $p(y|x,u)$. A local cost $c(x,u)$ is associated with each state and action. Preferentially, in an average reward setting, the aim of the AC algorithm is to find an optimal control policy in order to minimise the average expected cost per state over all states. This may be defined as:

$$\overline{a}(\theta) = \sum_{x \in X, u \in U} c(x, u) \eta_\theta(x, u) \quad (1)$$

where $\eta_\theta(x,u)$ the stationary probability of the Markov chain $\{X_k, U_k\}$.

The Critic

The Critic agent is responsible for the evaluation of the current control policy on the basis of approximation of an associated expected cost. One of the most powerful methods used for this purpose is temporal difference (TD) learning, in which the total expected cost of a process that starts at state x, takes as first action u and follows policy $\mu(u|x,\theta)$ that may be defined through the value and action-value functions $V_\theta(x)$ and $Q_\theta(x,u)$, respectively:

$$V_\theta(x) = E\left[\sum_{k=0}^{\infty} \gamma^k c(x_k, u_k) \middle| x_0 = x\right] \quad (2)$$

$$Q_\theta(x, u) = E\left[\sum_{k=0}^{\infty} \gamma^k c(x_k, u_k) \middle| x_0 = x, u_0 = u\right] \quad (3)$$

The value and action-value functions may satisfy the following equations:

$$Q_\theta(x, u) = c(x, u) + \gamma \sum_y p(y | x, u) V_\theta(y) \quad (4)$$

$$V_\theta(x, u) = \sum_u \mu(n | x, \theta)\left[c(x, u) + \gamma \sum_y p(y | x, u) V_\theta(y)\right] \text{ (Bellman Equation)} \quad (5)$$

For the given observed states, $x=x_{k-1}$, $y=x_k$ and action $u=u_{k-1}$, and the Bellman Equation (5) may reduce to:

$$V_\theta(x) = c(x,u) + \gamma V_\theta(y) \quad (6)$$

The Bellman's curse of dimensionality restricts the analytical solution of (6) in high dimensional spaces and requires the use of approximation methods. In the TD framework, the value function $V(x)$ may be approximated by a parameterized function $V_w(x)$ with $w \in R^K$. The most commonly used architecture for the parameterized function may be the linear approximation defined as:

$$\tilde{V}_0^w(x) = \sum_{i=1}^{K} w^i g_\theta^i(x) = w^T g_\theta(x) \quad (7)$$

where $g_\theta(x)$ is a vector of basis functions of dimension K. Notation $w^T$ denotes transpose. The approximation of the value function may be performed via the estimation of the TD error d defined as the deviation of the approximated value function $\tilde{V}^w(x)$ from its subsequent estimation $\tilde{V}^w(y)$:

$$d = c(x,u) + \gamma \tilde{V}_\theta^w(y) - \tilde{V}_\theta^w(x) \quad (8)$$

On the basis of the TD error, the parameter vector w may be updated according to the formula:

$$w_{k+1} = w_k + a_k d_k \sum_{n=0}^{k} \lambda^{k-n} \nabla_w \tilde{V}_\theta^w(x) = w_k + a_k d_k z_k \quad (9)$$

where $\alpha_k$ is a positive non-increasing learning rate sequence, $0 < \lambda < 1$ is constant and $z_k$ may be the eligibility vector defined as:

$$z_k = \sum_{n=0}^{k} \lambda^{k-n} g_\theta(x_n) \quad (10)$$

and may be updated according to the following formula:

$$z_{k+1} = \lambda z_k + g_\theta(x_{k+1}) \quad (11)$$

A similar process may be followed for the approximation of the action-value function $Q_\theta(x,u)$:

$$\tilde{Q}_\theta^r(x, u) = \sum_{i=1}^{L} r^i \varphi_\theta^i(x, u) = r^T \varphi_\theta(x, u) \quad (12)$$

where $\varphi_\theta(x,u)$ is the vector of basis functions and $r \in R^L$ is the respective parameter vector. A commonly used choice of the basis functions is $\varphi_\theta(x,u) = \psi_\theta(x,u)$, where $\psi_\theta(x,u) = \nabla_\theta \ln\mu(u|x,\theta)$ is the likelihood ratio derivative of the control policy.

The Actor

The aim of the Actor is to optimise the control policy over time towards minimisation of the average expected cost per state $\bar{\alpha}(\theta)$. Policy gradient methods may be employed for the minimisation, which involve the estimation of the gradient $\nabla_\theta \bar{\alpha}(\theta)$ with respect to the policy parameter vector $\theta$. The general policy update function may have the following form:

$$\theta_{k+1} = \theta_k - \beta_k \nabla_\theta \bar{\alpha}(\theta) \quad (13)$$

where $\beta_k$ is a positive sequence of learning rates. Various versions of Actor may be proposed, mainly distinguished by the approximation strategy for the gradient $\nabla_\theta \bar{\alpha}(\theta)$. In the present example, the Actor may be used in which:

$$\nabla_\theta \bar{\alpha}(\theta) = \sum_{x,y} \eta_\theta(x, u) d_t \psi_\theta(x, u) \quad (14)$$

Glucose Regulation in T1D Based on an AC Algorithm

Figure 3:
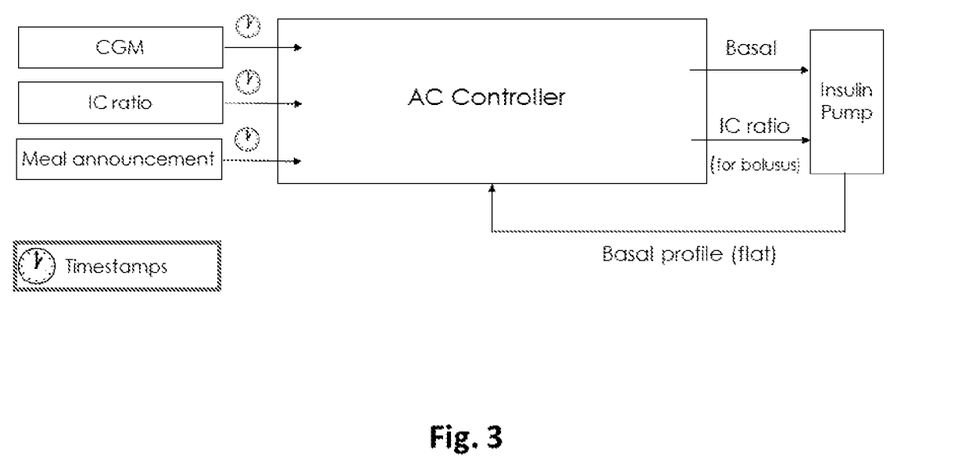
FIG. 3 is a block diagram illustrating the inputs/outputs of the actor-critic control system of FIG. 1 for the implementation of the closed-loop system according to the invention.

The AC algorithm is designed to optimise the insulin regime for each T1D patient. The insulin regime may be defined as the combination of insulin basal rate (BR) and insulin-carbohydrate (IC) ratio (FIG. 3). This choice was taken in order to be consistent with the medical practice; however, other insulin regime profiles may be used. The IC ratio is used for the calculation of the bolus dose ($I_{bolus}$) according to the known carbohydrate (CHO) size of the upcoming meal as:

$$IC = I_{bolus}/CHO \quad (15)$$

Prior to the design of the Critic and Actor gents, two important parameters of the algorithm need to be defined:
i) the learning window, which corresponds to the update rate of the algorithm and
ii) the state of the system.
Both are discussed in the following paragraphs.

Learning Window

Figure 4:
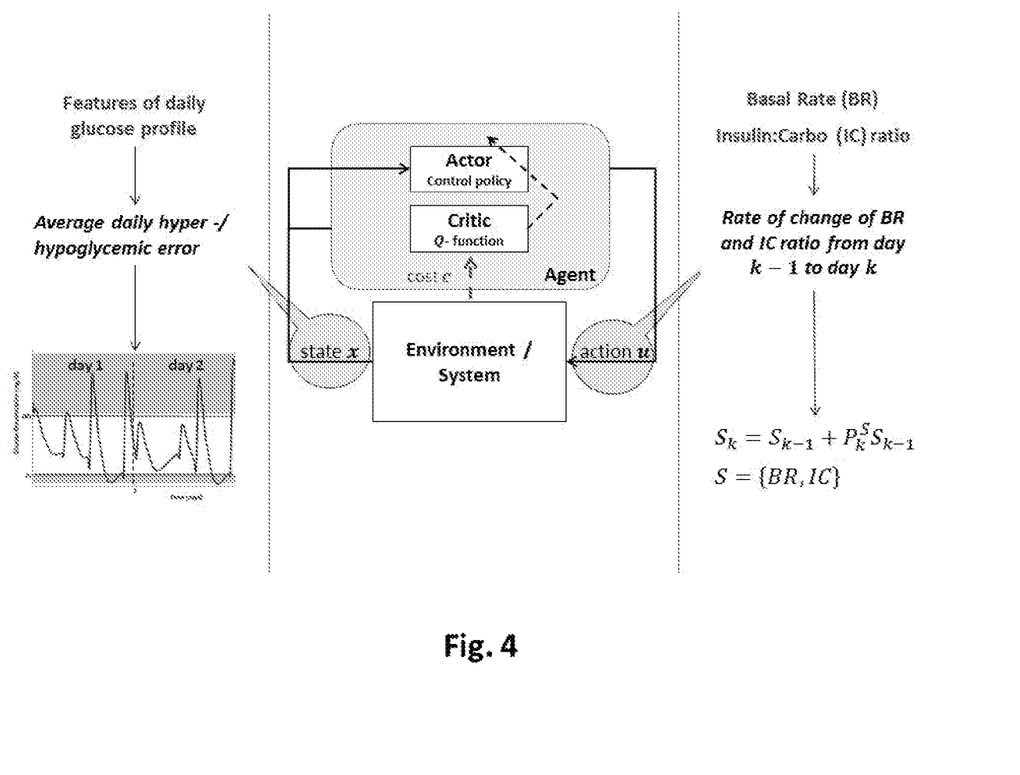
FIG. 4 is a block diagram illustrating one implementation of the actor-critic control system of FIG. 1 for the implementation of the closed-loop system according to the invention.

The learning window is defined here as the time period provided for data collection prior to an update of the insulin profile. There are several considerations that influence this decision. The learning window cannot be comparable to the loop delay introduced by the CGM and the subcutaneous insulin absorption. Moreover, the trade-off between fast and slow learning should be considered. Frequent updates may effectively follow the rapid glucose dynamics, but miss the "big picture" which carries more basic or generic information about the patient's characteristics. Taking these into account, this document describes an example where the optimisation window is one day (24 hours). It is understood that "one day" refers to a time period of 24 hours which may start at any time of day or night, preferentially the time period may start at midnight of a given day and may end at the end this given day. This time period may also be longer or shorter. This "1 day" choice also considers the 24-hour circle of the human body, which carries adequate information about the patient's general glycaemic status. As a result, the insulin policy is evaluated and updated once per day as based on the respective daily glucose profile (FIGS. 3 and 4).

State of the System

The dynamics of the glucoregulatory system are represented as a Markov decision process, where the state $x_k$, is the status of the system in terms of hypo- and hyperglycaemia for day k. The glucose error EG at each time t may be defined as:

$$EG(t) = \begin{cases} G(t) - G_h & \text{if } G > G_h \\ G(t) - G_l & \text{if } G < G_l \\ 0 & \text{else} \end{cases} \quad (16)$$

where G(t) is the glucose value at time t and $G_h$=180 mg/dl, $G_l$=70 mg/dl are the hyper- and hypoglycaemia bounds, respectively. The glycaemic profile of day k may be described by two features related to the hyper- and hypoglycaemic status of that day and more specifically to the average daily hypoglycaemia and hyperglycaemia error (FIG. 4):

$$x_k^1 = \frac{1}{N_1} \sum_{t \in day_k} H(EG(t)) \quad (17a)$$

$$x_k^2 = \frac{1}{N_2} \sum_{t \in day_k} H(-EG(t)) \quad (17b)$$

where H(•) is the Heaviside function and $N_i$ is the number of time samples above the hyperglycaemia (i=1) or below the hypoglycaemia (i=2) threshold. Firstly, the features are normalized in [0 1]. The normalized features formulate the state $x_K = [x_k^1 x_k^2]^T$ of day k.

Design of the Critic

The mathematical formulation of the Critic was given before. The CGM measures the blood glucose of the patient over the time period (for example 24 h) and these measurements define the glucose profile of the time period. All or a part of these data may be recorded in a memory device. At the end of day k (it is understood that the day is an example of the time period), the glucose profile of the day is collected (and may be retrieved from the memory device) and the state $x_k$ may be calculated, for example by taking into account the measurements of the blood glucose or the blood glucose profile. On the basis of the state, a local cost $c(x_k)$ may be assigned (FIG. 4), defined as:

$$c(x_k) = \alpha_h x_k^1 \alpha_l x_k^2 \quad (18)$$

The weights $\alpha_h$ and $\alpha_l$ are used for scaling the hypo- and hyperglycaemia components. $a_h$ and $a_l$ may be comprised between 0 and 50, for example $\alpha_h$=1 and $\alpha_l$=10. The action-value function is linearly approximated as described in (12). The basis functions $\varphi(\bullet)$ may be set equal to the likelihood ratio derivative (LRD) of the control policy which will be derived in a later phase. For the Critic update, the constants γ and λ may be comprised each of them between 0 and 1, preferentially γ=0.9 and λ=0.5 for all patients. The Critic's learning rate may be comprised between 0 and 1, preferentially $\alpha_k^c$=0.5 for all patients. These values were found experimentally. The initial parameters $r_0$ may be set to random values in [−1 1] and the initial parameters $z_0$ to zero values for all patients.

Design of the Actor

The Actor implements a dual stochastic control policy $\mu(u_k|x_k,\theta_k)$ for the daily optimisation of the BR and IC ratio starting from an initial BR (IC ratio) value (FIG. 4). In order to dissociate the action from the absolute level of the current insulin regime, the control action $u_k$ may be defined as the rate of change of BR (IC ratio) from day k−1 to day k. The benefit of this choice will be revealed later. Thus, the BR (IC ratio) may be updated as follows:

$$S_k = S_{k-1} + P_k^S S_{k-1} \quad (19)$$

$$P_k^S = u_k^S \sim \mu(u_k^S|x_k,\theta_k^S) \quad (20)$$

where S={BR, IC}, $S_k$ is the control policy for the day k and $P_k^S$ is the control action i.e. the rate of change of $S_k$ from day k−1 to day k. The final applied control action $P_k^S$ is withdrawn from the probability distribution $\mu(u_k^S|x_k, \theta_k^S)$ of the control policy based on the current state $x_k$ and policy parameter vector $\theta_k^S$. Preferentially, for the design of the probability distribution, a three-step process is followed, based on the generation of three different types of control actions:

i) linear deterministic,
ii) supervisory and
iii) exploratory action.

However, only one or two of these types of control actions may be used for the design of the probability distribution. Hereafter, the notations k and S are omitted for clarity purposes. The procedure may be the same for BR and the IC ratio.

Linear deterministic control action:

The linear deterministic control action $P_a$ is defined as the linear combination of the current state and policy parameter vector:

$$P_\alpha = x^T\theta \quad (21)$$

In other words, this control action associates the daily hypo- and hyperglycaemic status to the needed percentage of BR (IC ratio) change for the next day.

Supervisory control action:

The supervisory control action $P_s$ is a conservative rule-based advice to the algorithm and mainly serves as guidance of the direction of change to be followed and as a safety module against extreme insulin changes by the algorithm. The supervisory action is defined as:

$$P_s = \begin{cases} 0 & \text{if } x_1 = x_2 = 0 \\ \pm 0.1x_1 & \text{if } x_1 > 0 \text{ and } x_2 = 0 \\ \mp 0.1x_2 & \text{if } x_2 > 0 \end{cases} \quad (22)$$

where the upper sign refers to BR and the lower sign to IC ratio.

Preferentially, the weighted sum of the two previous actions may define the total deterministic control action $P_d$:

$$P_d = hP_\alpha + (1-h)P_s \quad (23)$$

where h is a factor that allows us to scale the contribution of each part to the final output. h may be comprised between 0 and 1. For example, in this document, the weighting factor has been chosen as h=0.5 and thus assigns equal contributions to the two actions.

Exploratory control action:

The exploratory control action $P_e$ may occur by adding white noise to the final deterministic policy as below:

$$P_e = P_d + N(0,\sigma) \quad (24)$$

where N(0, σ) may be white Gaussian noise with zero mean and standard deviation σ. The aim of the exploration process is to widen the search space of the algorithm in order to optimise the performance and the convergence rate. The result of the exploration process is the final control action to be applied.

Based on the previous analysis, we are now ready to derive the control policy μ(u|x,θ) as the probability distribution from which the final control action u=$P_e$ is withdrawn:

$$\mu(u \mid x, \theta) = \frac{1}{\sigma\sqrt{2\pi}} \exp\left(-\frac{1}{2}\left(\frac{u - P_d(x)}{\sigma}\right)^2\right) \quad (25)$$

The control policy is a Gaussian probability distribution with mean equal to the total deterministic action $P_d(x)$ and standard deviation σ. Finally, the LRD $\psi_\theta(x,u)$ has to be derived. Taking the gradient of the control policy with respect to θ we have:

$$\nabla_\theta \mu(u \mid x, \theta) = \mu(u \mid x, \theta) \frac{u - P_d(x)}{\sigma^2} \nabla_\theta P_d(x) \quad (26)$$

From (25, 26), LRD becomes:

$$\psi_\theta(x, u) = \nabla_\theta \ln\mu(u \mid x, \theta) = \frac{u - P_d(x)}{\sigma^2} \nabla_\theta P_d(x) \quad (27)$$

and the policy parameter update of the Actor is defined as follows:

$$\theta_{k+1} = \theta_k - \beta_k d_k \psi_{\theta_k}(x_k, \mu_{\theta_k}(u_k \mid x_k)) = \theta_k - \beta_k d_k \frac{u - P_d(x)}{\sigma^2} \nabla_\theta P_d(x) \quad (28)$$

It can be seen in (28) that the update of the policy parameter vector depends on the difference between the total deterministic and the exploratory policy, i.e. on the noise variance $\sigma^2$. When an optimal policy has been found, which results in a state $x_k \sim 0$, we would like to reduce the exploration, as this may lead the system away from the solution found. To this end, the variance $\sigma^2$ is defined as a function of the state $x_k$:

$$\sigma^2 = KS\|X_k^2\| \quad (29)$$

The larger the state $x_k$, the greater the time spent in hypo-/hyperglycaemia on day k, i.e. the larger the exploration space for a better control policy. The constant KS may be comprised between 0 and 1, preferentially set to 0.05 (following a trial-and-error process). The Actor learning rate $\beta_k$ may be set equal to the variance $\sigma^2$ using the same reasoning. In this way, the AC algorithm may be all-time learning, in order to compensate for temporal or permanent changes in the gluco-regulatory system of each patient.

Personalized Tuning of the AC Algorithm

Figure 5:
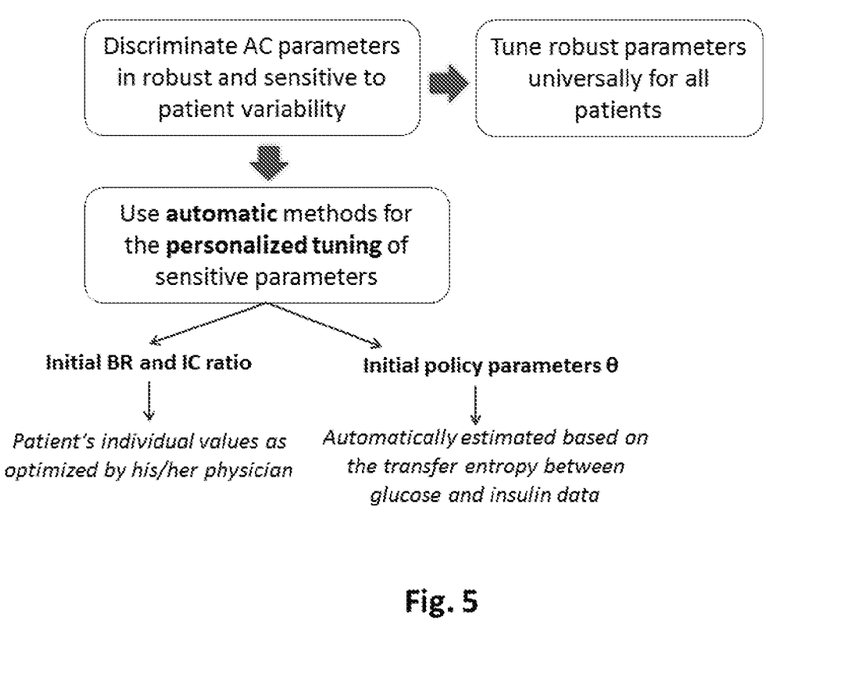
FIG. 5 illustrates an example of the procedure to be followed to tune the actor-critic system according to the invention.

The design of the AC algorithm, as described in the previous section, involves various parameters that need to be tuned (FIG. 5). Taking into account the patient variability, personalized tuning might be required for some of the parameters. Manual tuning for each patient is infeasible or might compromise the patients' safety, so automatic methods need to be investigated.

On the basis of preliminary simulations and under different tuning configurations, the AC parameters may be first split into two classes, as robust (R) or sensitive (S):

The parameters included in the R class were associated with low sensitivity to patient variability and may be manually tuned by empirical methods, with common values for all patients given in the previous section.

The S class included the parameters which were found to be sensitive to patient-specific characteristics. The parameters identified in this class may be the initial values of the BR and IC ratio and the Actor's initial policy parameter vector $\theta_0$. For the first two parameters, universal tuning is not possible, as the insulin requirements naturally differ between different diabetic patients. It will be shown that the policy parameter vector θ may be tightly related to patient-specific characteristics and its initial tuning affects both the performance and convergence rate of the algorithm. Thus, automatic, individualized tuning procedures may be followed for the S class parameters. Table 1 summarises an example of parameters of the AC algorithm along with their description, values and tuning class.

TABLE 1

Example of parameters of the AC algorithm

| Parameter | Description | Value | Class |
|---|---|---|---|
| $a_h$ | Local cost hyperglycemia weight | 1 | R |
| $a_l$ | Local cost hypoglycemia weight | 1 | R |
| γ | Discount factor long-term cost | 0.9 | R |
| λ | TD learning constant | 0.5 | R |
| $a_k^C$ | Critic learning rate | 0.5 | R |
| $a_k^A$ | Actor learning rate | 1 | R |
| $r_0$ | Critic initial parameter vector | Random in [−1 1] | R |
| $z_0$ | Critic initial eligibility vector | Zero | R |
| σ | Standard deviation exploration action | 0.05 | R |
| $S_0$ | Actor initial BR/IC ratio | patient-specific | S |
| $\theta_0$ | Actor initial parameter vector | patient-specific | S |

Initialization of BR and IC Ratio

In order to guarantee safety, the initial values for the BR and IC ratio should be specific and appropriate for each patient. Clinical experience in treating diabetes has developed a number of empirical rules for the estimation of BR profiles and IC ratios for patients under CSII pump therapy, as based on their body weight, SI and lifestyle factors. These rules provide an open-loop insulin regime which may not be optimal but ensures primary glucose regulation. Thus, when applied in clinical practice, the BR and IC ratio of the AC algorithm can be initialized using the patient's individual values as optimised by his/her physician (FIG. 5). This practice has the additional advantage that the transition of a patient from CSII to AP can be smoother both for him/herself and the physician.

Initialization of Policy Parameter Vector θ

Initialization of the policy parameter vector θ may be based on investigation of its natural representation within the designed insulin infusion control algorithm (FIG. 5). The optimal values of the policy parameter vector θ answers the question: "How much should we change BR and IC ratio based on the observed daily hyper-/hypoglycaemia?" The answer may be related to the patient's SI and depends on his/her body mass index (BMI), total daily insulin (TDI) needs, lifestyle and genetic factors.

Estimation of SI is currently performed in a clinical environment using clamp or intravenous glucose tolerance tests, which are time consuming and costly. In recent years, there have been efforts to achieve online estimation of SI to be incorporated into AP algorithms, using CGM and insulin pump data and based on the inverse solution of a diabetes physiological model.

Often in practice, SI is directly related to a patient's TDI, as this information is easily accessible. However, even for two patients with the same TDI and BMI, the impact of 1 U of insulin may be different. In this study, we capture this difference through the IT from insulin to glucose signals. The insulin-to-glucose IT may be measured using the notion of transfer entropy (TE), a very powerful method for the estimation of IT in non-linear random processes. TE estimates the IT from a cause signal Y (insulin) to an effect signal X (glucose). This value is independent of the magnitude of the two signals, i.e. the amount of insulin and the glucose concentration. For two patients with the same TE, higher TDI corresponds to lower SI. Similarly, if two patients have the same TDI, higher TE can be translated to lower SI. Following this reasoning, information about a patient's SI may be estimated as:

$$\tilde{SI} = c_1 \frac{TE}{TDI} \quad (30)$$

where $c_1$ is a positive constant. Given the definition of SI, if a patient wants to reduce his/her glucose levels by $\Delta G$, the necessary amount of insulin should be:

$$I_{\Delta G} = \frac{\Delta G}{SI} \quad (31)$$

Substituting SI with its estimation $\tilde{SI}$ given in (30), we have:

$$I_{\Delta G} = c \frac{\Delta G}{TE} TDI \quad (32)$$

where $c=1c_1$.

In the case of the AC algorithm, the aim is to find the optimal change in the BR and IC ratio in order to eliminate daily hypo- and hyperglycaemia. This can be seen as a parallel to (32):

$$\Delta S^i = c' \frac{x^i}{TE} TDI \quad (33)$$

where $x_i$ is the hyperglycaemia (i=1) or hypoglycaemia (i=2) feature, i.e. the average daily hypo-/hyperglycaemic error as defined in (29a, b), $\Delta S^i$ is the change in BR or IC ratio based on the respective feature and c' a positive constant. Considering that TDI is directly reflected in the daily BR and IC ratio, (33) can be rewritten as:

$$\Delta S^i = c' \frac{x^i}{TE} S \quad (34)$$

If we set $$\theta^i = \frac{c'}{TE},$$

(34) becomes:

$$\Delta S^i = \theta^i x^i S \quad (35)$$

and the total change in BR or IC ratio based on both hypo- and hyperglycaemia features is the linear combination of their respective contributions as:

$$\Delta S = \Delta S^1 + \Delta S^2 = \theta^1 x^2 S = (\theta^1 x^1 + \theta^2 x^2)S = \theta^T x S \quad (36)$$

where $\theta=[\theta_1\ \theta_2]^T$ and $x=[x_1\ x_2]^T$ is the feature vector. Finally, if we set $P_S=\theta^T x$ then (35) becomes:

$$\Delta S = P^S S \quad (37)$$

where $P^S$ is the percentage of change of S and represents AC deterministic control action as previously defined in (33).

The aforementioned analysis illustrates that defining the control action as the rate of insulin change permitted tuning of AC, using the insulin to glucose IT and without the need to estimate SI, which would be a more cumbersome process. The analysis may be approximate and may (only) be used as a draft estimate of the necessary BR or IC update. However, the scope is to provide a better starting point to AC in order to enhance the optimisation process. The initial values of the policy parameter vector for patient p may be set as:

$$\theta_0^S(p) = \left[ \frac{W_h}{TE(p)} \quad \frac{W_l}{TE(p)} \right] \quad (38)$$

where $W_h$ and $W_l$ are weights related to the hyper- and hypoglycaemia features and may be comprised between −1 and 1, preferentially $W_h=0.1$ and $W_l=-0.2$ for all patients. Again, a higher value is assigned to the hypoglycaemic weight, as avoiding hypoglycaemia has higher priority.

Estimation of Insulin-to-Glucose TE

Insulin-to-glucose TE may be estimated on the basis of CGM and insulin pump data for four days (for example) collected from each patient. In order to choose the appropriate data size, datasets of different durations were used and the correlation between the respective TE values was computed for successive data lengths. It was observed that data of four days or more gave highly correlated TE values (>99%), The estimation of TE may be based on the following formula:

$$TE_{IA \to G} = \sum_t p(G_t, G_{t-1}, IA_{t-d}) \log \frac{p(G_t \mid G_{t-1}, IA_{t-d})}{p(G_t \mid G_{t-1})} \quad (39)$$

where $G_t$, $IA_t$ are the glucose and active insulin at time t and d is the insulin time-delay set here as d=20 minutes, according to the average physiological insulin absorption delay for rapid-acting insulin analogues. Active insulin may be estimated as the sum of insulin on board (IOB) related to the bolus doses and basal insulin infusion:

$$IA(t) = IOB(t) + I_{basal}(t) \quad (40)$$

For the estimation of the probability distributions, the fixed data partitioning method may be used, in which the time-series may be partitioned into equal sized bins and the probability distributions are approximated as histograms.

The size of the partition bins for glucose and insulin may be $G_{bin}=10$ mg/dl and $IA_{bin}=1$ U, respectively.

General Concepts of the Invention

According to one aspect as described above, the invention provides a method for estimating an insulin therapy comprising at least one of the insulin infusion rate (basal) and insulin to carbohydrate ratio (bolus dose=carbohydrates contained in the upcoming meal x insulin to carbohydrate ratio) adapted to a patient based on one of the following items:

adaptive controller using actor-critic learning;

insulin control policy evaluated (critic) and updated (actor) once per day using the glucose/insulin profiles of the last 24 hours;

the state of the glucose-regulatory system as described by two features related to the hyper- and hypoglycaemic status of that day and more specifically by the average daily hypoglycaemia and/or hyperglycaemia error;

the evaluation of the control policy (critic) at the end of each day based on the calculation of glucose-regulatory system's state and the corresponding assigned local cost, preferentially using temporal difference learning; and the update of the control policy (actor), the rate of insulin change from a first time period (in the example one day) to a subsequent time period, based on the effects of one, two or three different types of control actions, i) the deterministic action, which associates the daily hypo- and hyperglycaemic status to the needed percentage of basal rate and insulin to carbohydrate ratio change for the next day, ii) the supervisory action, which corresponds to the conservative suggestion of the control policy and acts as safety and guidance to the system, and iii) the exploratory action, which widens the search space of the system's status and supports the faster and better converge; or Scope of the actor is to minimize the average expected cost per system's state (optimization of the control policy)

The method may include two successive stages:

Initialization stage, in which the method is initialized;

Learning stage, in which the adaptive method learns from the patient (patient-specific control policy).

Preferentially the learning stage is continuous and is executed at each time period after the initialization stage.

The actor's initial basal insulin rate, initial insulin to carbohydrate ratio and/or the policy parameter vector may be patient-specific.

The basal insulin rate and insulin to carbohydrate ratio of the AC may be initialized using the patient's individual values as optimised by his/her physician and/or an in silico simulator.

The policy parameter vector of the AC controller may be initialized using the insulin-to-glucose transfer entropy estimated on the basis of glucose and insulin pump data for a short period of time, e.g. four days, collected from each patient.

Insulin may be an insulin analog.

The method may be carried out prior/during/after delivering insulin to the patient.

The method may receive wireless/wired communication interfaces real-time data from a glucose monitor and insulin pump.

The meal may be unannounced or manually entered by the patient.

The meal may be announced to the controller via interface with other mobile/smartphone applications or sensors.

The estimated basal rate and insulin to carbohydrate ratio may be used to control an insulin pump or an insulin patch pump either directly or via the pump's control unit.

In a further aspect, the invention provides a device for informing the patient regarding the estimated basal rate and insulin to carbohydrate ratio. The device can be any portable/mobile device or smartphone with processor configured to execute the method described herein above.

The device may include all the display and interfaces needed to inform the patient about the optimal insulin therapy and transfer wired/wireless the data to a cloud/server or other diabetes technology related devices.

The device may include interfaces with other mobile applications (e.g. diabetes e-logbook, fitness/food apps etc).

The device may include all the display and interfaces needed to inform the patient about the optimal insulin therapy and transfer wired/wireless the data to a cloud/server or other diabetes technology related devices,

The invention claimed is:

1. A method for determining and applying an insulin therapy for a patient, the method comprising the steps of:

using a reinforcement learning algorithm with a specially programmed data processor, the using including,
 (a) a non-human critic which evaluates an insulin control policy including at least one of an insulin infusion rate and an insulin to carbohydrate ratio, and
 (b) a non-human actor which improves the insulin control policy;

administering, over a predetermined period of time, a predetermined insulin control policy to the patient with an insulin infusion device;

collecting, over the predetermined period of time, blood glucose data of the patient with a blood glucose measurement device;

determining a state of a glucose-regulatory system of the patient based on the collected blood glucose data from the step of collecting;

evaluating by the critic the predetermined insulin control policy based on the state of the glucose-regulatory system;

updating the insulin control policy by the actor with the data processor, based on a determined control action, the updated insulin control policy including at least one of an updated insulin infusion rate and an updated insulin to carbohydrate ratio; and administering the updated insulin control policy over a subsequent period of time to the patient with the insulin infusion device, wherein the determined control action takes into account at least one of the following control actions,
 a linear deterministic control action including a linear combination of the glucose-regulatory system's state and a determined policy parameter vector,
 a supervisory control action including a conservative suggestion of a previous insulin control policy and acts as safety module against extreme changes of the insulin control policy by the algorithm and/or as guidance of the direction of the update, and
 an exploratory control action widening the search space of a state of the glucose-regulatory system and/or supports a faster converge.

2. The method according to claim 1, wherein the determined control action is defined as a rate of change of the insulin control policy from the predetermined period of time to the subsequent period of time.

3. The method according to claim 1, wherein the determined control action takes into account at least two of the linear deterministic control action the supervisory control action and the exploratory control action.

4. The method according to claim 1, wherein the determined control action takes into account a total deterministic control action which is determined by a mathematical model that takes into account the linear deterministic control action and the supervisory control action.

5. The method according to claim 4, wherein the exploratory control action is determined by a mathematical model that takes into account at least the total deterministic control action.

6. The method according to claim 1, wherein the critic evaluates the state of the glucose-regulatory system described by two features related to the hyper- and hypoglycaemic status occurred during the predetermined period of time.

7. The method according to claim 1, wherein the critic evaluates the state of the glucose-regulatory system described by the average daily hypoglycaemia and hyperglycaemia error occurred during the predetermined period of time.

8. The method according to claim 1, wherein the critic further computes a local cost of the state of the glucose-regulatory system for the predetermined period of time.

9. The method according to claim 8, wherein the actor is configured to minimize an average expected cost per state.

10. The method according to claim 1, wherein the evaluation step is performed at an end of each period of time.

11. The method according to claim 1, wherein the policy parameter vector depends on the difference between the total deterministic control action and the exploratory control action.

12. The method according to claim 1, wherein the policy parameter vector is updated at the end of the determined period of time.

13. The method according to claim 1, wherein the initial insulin control policy is determined by taking into account the patient's individual values as optimized by his/her physician and/or an in silico simulator.

14. The method according to claim 1, wherein the value or the initial value of the policy parameter vector is determined by using an insulin-to-glucose transfer entropy calculation.

15. The method according to claim 14, wherein the insulin-to-glucose transfer entropy is estimated on the basis of blood glucose data and insulin delivery data for a duration of a time period comprised between 1 and 7 days.

16. The method according to claim 1, further comprising an initialization phase during which an initial insulin control policy and/or an initial value of the policy parameter vector are determined and adapted to the patient.

17. The method according to claim 16, wherein the duration of the initialization phase is between 1 and 7 days.

18. The method according to claim 17, wherein the duration of the initialization phase is preferentially 4 days.

19. The method according to claim 1, wherein the duration of the predetermined period of time and/or of the subsequent period of time is between 1 hour and 36 hours.

20. The method according to claim 19, wherein the duration of the predetermined period of time and/or of the subsequent period of time is substantially equal to 24 hours.

* * * * *